United States Patent [19]

McSpadden

[11] Patent Number: 5,104,316
[45] Date of Patent: Apr. 14, 1992

[54] ENDODONTIC INSTRUMENT

[76] Inventor: John T. McSpadden, 6918 Shallowford Rd., Chattanooga, Tenn. 37421

[21] Appl. No.: 511,092

[22] Filed: Apr. 19, 1990

[51] Int. Cl.⁵ ............................................. A61C 5/02
[52] U.S. Cl. .................................. 433/102; 433/224
[58] Field of Search ................................. 433/102, 224

[56] References Cited

U.S. PATENT DOCUMENTS

| 2,453,696 | 11/1948 | Brooks | 433/102 |
| 4,299,571 | 11/1981 | McSpadden | 433/102 |
| 4,332,561 | 6/1982 | McSpadden | 433/102 |
| 4,850,867 | 7/1989 | Senia et al. | 433/102 |

FOREIGN PATENT DOCUMENTS

| 0648688 | 8/1937 | Fed. Rep. of Germany | 433/102 |
| 2524102 | 1/1976 | Fed. Rep. of Germany | 433/102 |
| 2754098 | 6/1978 | Fed. Rep. of Germany | 433/102 |
| 0670756 | 7/1989 | Switzerland | 433/102 |
| 0682372 | 11/1952 | United Kingdom | 433/102 |

Primary Examiner—Gene Mancene
Assistant Examiner—Adriene B. Lepiane
Attorney, Agent, or Firm—Luedeka, Hodges, Neely & Graham

[57] ABSTRACT

An endodontic reamer or file instrument for cleaning and shaping root canals includes a shank having a tapered working portion extending along a section of the shank length to a leading end. A pilot is attached to the working portion adjacent the leading end and is smaller in diameter than is the working portion at the leading end. The working portion includes at least one continuous helical flute which spirals along its length and a helical land at the periphery of the working portion which extends between adjacent flutes. The working portion also includes at least one lip adjacent the pilot which has a cutting edge which lies generally in a radial plane of the shank, and each flute which spirals along the length of the working portion toward the leading end terminates at the cutting edge of a corresponding lip so that as the instrument is moved longitudinally through a root canal, root canal tissue disposed to one side of the pilot is exposed to the cutting edge of the working portion.

5 Claims, 2 Drawing Sheets

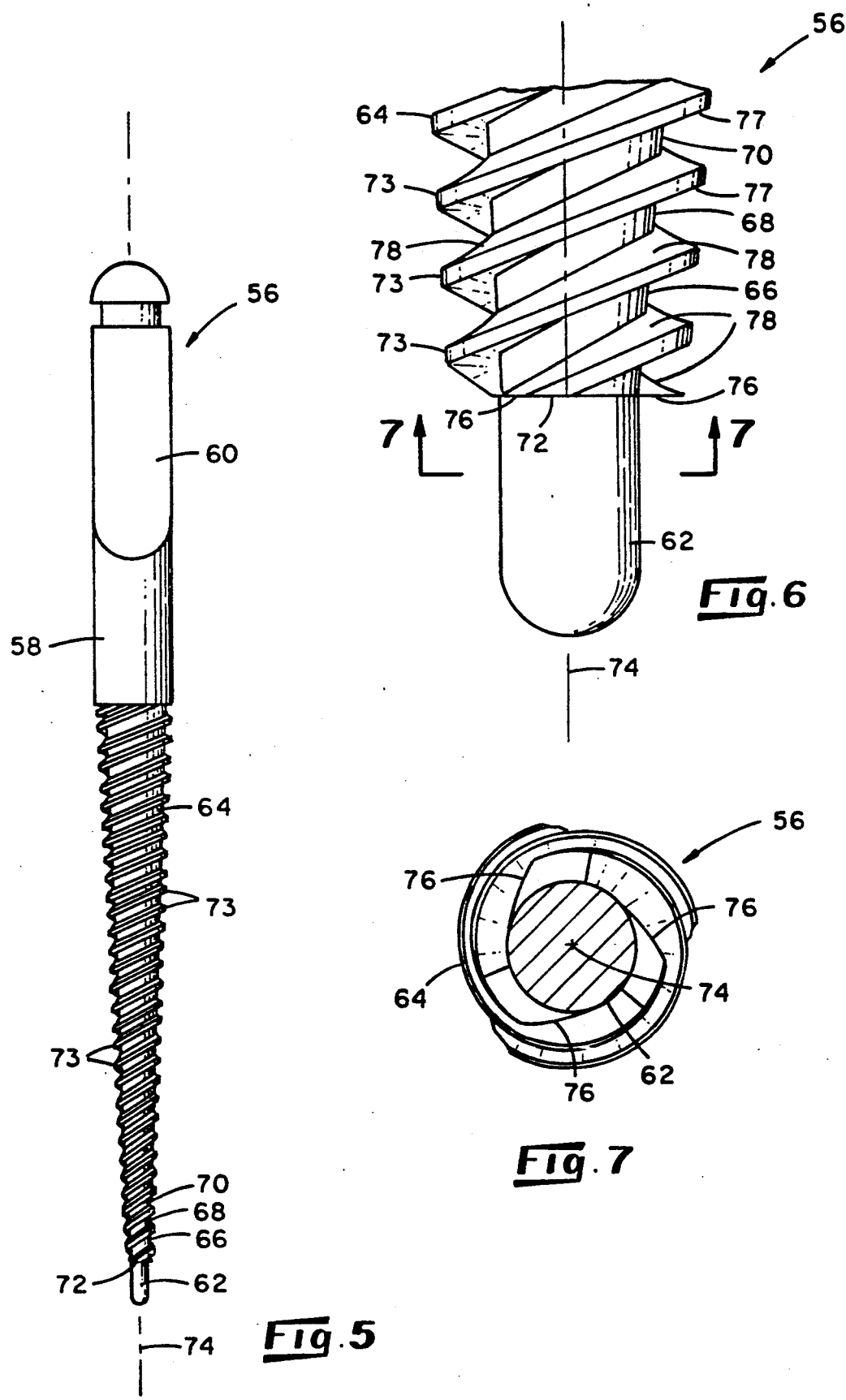

ENDODONTIC INSTRUMENT

BACKGROUND AND SUMMARY OF THE INVENTION

The present invention relates generally to the field of instruments and relates more particularly to endodontic reamers and files used for cleaning and shaping root canals.

In order to remove decayed, injured or dead tissue from the root canal of a tooth, an endodontist will first drill into the tooth to locate the root canal and thereafter use instruments of small diameter, such as reamers and files, to remove the decayed, injured or dead tissue from the canal. The goal of tissue removal with the instrument is to produce a funnel-shaped canal, with the smaller end at the apical foramin, so as to provide the canal with a desirable form for filling. Since root canals are not necessarily straight, the instrument must be able to follow a curved path as it is moved through the canal for purposes of removing the tissue. Therefore, the instrument must be flexible yet possess sufficient strength so that it is not easily broken when moved through a root canal.

Commonly, both files and reamers have flutes which spiral along a portion of the instrument length, and whether the instrument is a file or a reamer is determined by the pitch of the flutes. A greater pitch enables the instrument to cut better in a rotary mode, hence a reamer, and a lesser pitch enables the pitch to cut better in the reciprocating mode, hence a file. During a cleaning and shaping operation performed with such a file or reamer, the instrument is normally rotated and moved into and out of the root canal along the longitudinal axis of the instrument. Therefore, even during rotational movement of a reamer through a canal, the instrument is commonly reciprocated to a degree to effect the desired cut. Similarly, a file is commonly rotated slightly as it is reciprocated longitudinally.

In order that the instrument cut into root canal tissue as it is rotated and moved longitudinally, relatively high torsion forces must be typically applied to the instrument. This translates into relatively high torsional loads on the instrument and may lead to torsional failure of the instrument. In addition, the curved path of common root canals which requires that the instrument concurrently be subjected to bending and torsional loads as it is moved along the canal increases the likelihood of torsional failure.

Accordingly, it is an object of the present invention to provide an improved endodontic instrument, such as a reamer or file, which requires that only a relatively small amount of torsion force be applied in order that the instrument be simultaneously rotated and moved along its longitudinal axis through a root canal.

Another object of the present invention is to provide such an instrument which provides a relatively clean cut when moved in cutting relationship with root canal tissue.

More particularly, the present invention provides an endodontic instrument, such as a reamer or file, having an elongated shank having a working, or cutting, portion which extends along a section of the length of the shank and includes a leading end. The shank also includes a pilot attached to the working portion at the leading end thereof so as to be arranged coaxially with the working portion and which is smaller in diameter than the diameter of the working portion at the leading end. The working portion includes at least one continuous helical flute which spirals along the length of the working portion and extends between adjacent flutes and further includes at least one lip adjacent the pilot which has a cutting edge which generally lies in a radial plane of the shank. Each flute which spirals along the length of the working portion terminates at the cutting edge of a corresponding lip so that as the instrument is moved longitudinally through a root canal, root canal tissue disposed to one side of the pilot is exposed to the cutting edge of the working portion.

A more complete understanding of the present invention will be had by reference to the specification and accompanying drawings wherein like numerals refer to like parts throughout.

BRIEF DESCRIPTION OF THE DRAWINGS

FIG. 5 is a diagrammatic view similar to that of FIG. 1 of another embodiment of a dental instrument embodying features of the present invention;

FIG. 6 is a view similar to that of FIG. 5 of the lower portion of the FIG. 5 instrument but drawn to a slightly larger scale; and FIG. 7 is a cross-sectional view taken along line 7—7 of FIG. 6.

DETAILED DESCRIPTION OF THE ILLUSTRATED EMBODIMENTS

The figures diagrammatically illustrate a dental instrument used as a file or reamer for removing tissue from the root canal of a tooth. As mentioned earlier, whether the instrument is a file or a reamer is determined by the pitch of the helical flutes. A greater pitch enables the instrument to cut better in the rotary mode, hence a reamer, and a lesser pitch enables the instrument to cut better in the reciprocating mode, hence a file. The principles of the present invention may be applied to both dental files and reamers.

Figure 1:
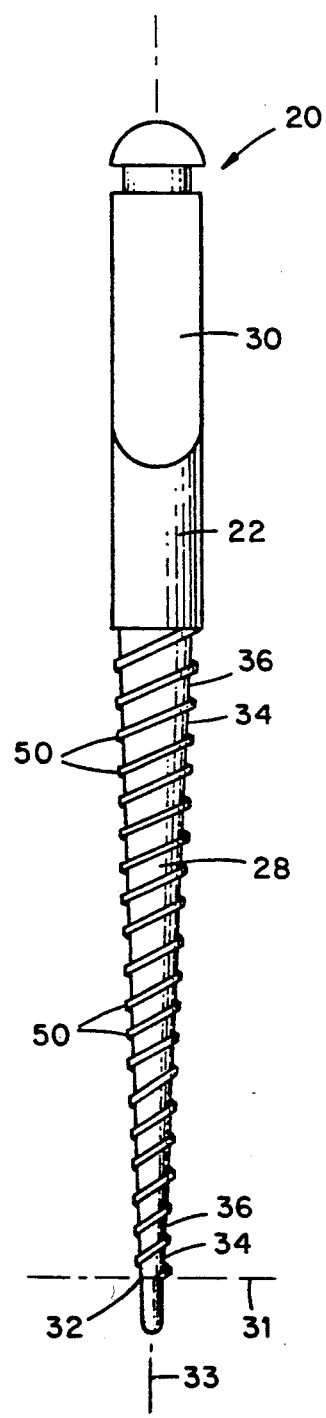
FIG. 1 is a diagrammatic side view of one embodiment of a dental instrument embodying features of the present invention.

With reference to FIG. 1, the instrument, indicated as 20, includes a shank 22 having a working portion 28 which is tapered along a portion of the length of the shank 22 to a pilot 26. The instrument 20 is constructed out of flexible stainless steel, as required by standards, which enables the instrument to flex along its length as the instrument 20 is directed longitudinally along a root canal. The working portion 28 and pilot 26 of the instrument 20 are integrally formed as a unit.

The upper end of the shank 22 is illustrated in FIG. 1 as being substantially cylindrical in shape. A fitting 30 is formed in the upper cylindrical part of the shank 22 for connection to a standardized handle (not shown) for manual manipulation of the instrument 20 or to mate with a chuck of a dental handpiece (not shown).

Figure 2:
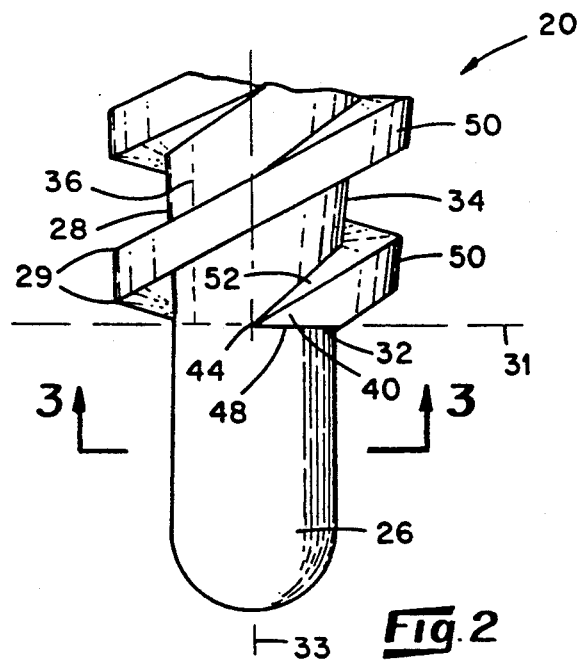
FIG. 2 is a view similar to that of FIG. 1 of the lower portion of the FIG. 1 instrument but drawn to a slightly larger scale.

The working portion 28 of instrument 20 extends for a substantial distance along the length of the body 22 and possesses a generally tapered form as a path is traced from the upper end of the working portion 28 to a lower leading end, indicated as 32, of the working portion 28. More specifically, the working portion 28 possesses a diameter which decreases in size from the upper end of the working portion 28 to the leading end 32 wherein the working portion diameter at any radial cross section is twice its largest radius. In accordance with acceptable standards, the working portion 28 possesses a uniform taper wherein the working portion diameter decreases by about 0.02 mm for every one mm of instrument length. As best shown in FIG. 2, the leading end 32 of the working portion 28 is arranged in a plane 31 oriented generally perpendicular to the longitudinal axis 33 of the instrument 20.

The working portion 28 also includes two helical flutes 34, 36 which spiral along the length of the working portion 28 from the holding portion 24 to the leading end 32. Each flute 34 or 36 has a wall which meets an adjacent land, described in greater detail herein, along a peripheral cutting edge 29 (FIG. 2) at the periphery of the working portion 28. Although the flutes 34, 36 may possess any of a number of configurations or cross-sectional shapes which provide these peripheral cutting edges 29 with any of a variety of cutting rake angles, it is preferred that each the peripheral cutting edge 29 is provided with a neutral cutting rake.

It will be understood that in accordance with the broader aspects of this invention, the flute pitch and helical angle of the flutes of the working portion may differ between instruments. For example, the working portion of one instrument may possess a constant pitch while another instrument may possess a constant helical angle. Standards exist which prescribe such flute characteristics so that the resulting working portion provides an effective cutting surface, and it is to these standards that the instrument 20 conforms. For exemplary purposes, the width of the flutes 34, 36 of the instrument 20 is constant along the working portion length and is within the range of about 0.0015 to 0.0035 inches.

Figure 3:
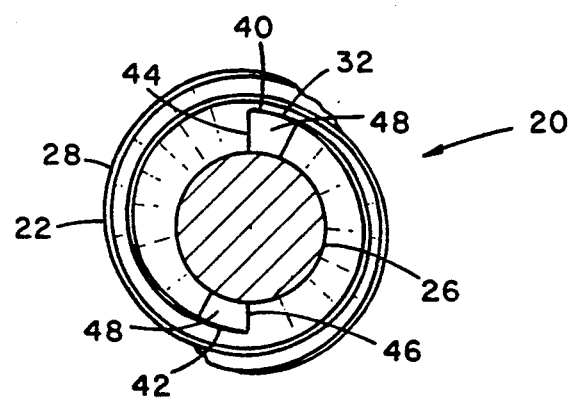
FIG. 3 is a cross-sectional view taken along line 3—3 of FIG. 2.

The pilot 26 is in the form of a smooth elongated section joined to the leading end 32 of the working portion 28 so as to be axially aligned with the pilot 26 along the longitudinal axis 33. The pilot 26 is cylindrical in shape along a major section of its length and terminates at a free end which is rounded in shape. The pilot 26 may extend from the leading end 32 of the working portion 28 for any convenient length, e.g., about 1.0 to 3.0 mm, so that as the instrument 20 is guided longitudinally through a root canal, the pilot 26 reduces the likelihood that the canal walls will be zipped by the instrument 20. As best seen in FIG. 3, the diameter of the pilot 26 is smaller than the diameter of the leading end 32. In the illustrated instrument 20, the diameter of the pilot 26 is about sixty to eighty percent that of the leading end 32.

Figure 4:
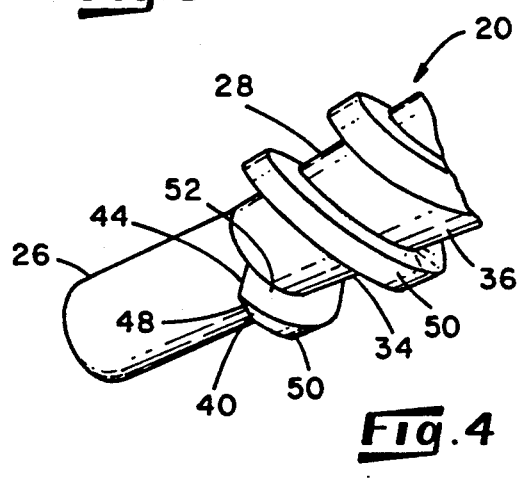
FIG. 4 is a fragmentary perspective view of the portion of the FIG. 1 instrument illustrated in FIG. 2.

It is a feature of the instrument 20 that the working portion 28 includes a pair of lips 40, 42 adjacent the pilot 26 which defines linear cutting edges 44, 46, respectively, which lie substantially in a radial plane (i.e., plane 31) of the instrument 20 and are positioned on opposite sides of the shank 22. As exemplified by the lip 40 illustrated in FIG. 4, each lip 40 or 42 is provided by a wedge-shaped portion of the working portion 28 located at the end of each flute 34 or 36 so that each lip 40 or 42 has a planar surface 48 (FIG. 3) which lies in the plane 31 of the leading end 32 and a sloped surface 52 (FIG. 4) which is provided by a wall of a corresponding flute 34 or 36. Thus, one side of the cutting edge 42 or 44, or the lower side as viewed in FIG. 2, is provided by the planar end surface 48 of the working portion 28 and the other side of the cutting edge 42 or 44, or the upper side as viewed in FIG. 2, is provided by the sloped flute surface 52.

With the cutting edges 42, 44 extending radially outwardly from the periphery of the pilot 24 as viewed in FIG. 2, the cutting edges 42, 44 are exposed to root canal tissue disposed to one side of the pilot 26 as the instrument 20 is moved longitudinally through a canal. When moving the instrument 20 so that the cutting edges 42, 44 move in cutting engagement with root canal tissue, only a relatively small amount of torsion forces must be applied to the instrument 20 in order to rotate the instrument 20 as it is moved longitudinally through the canal. Therefore, any need for the application of large torsion forces to the instrument 20 which may ultimately lead to torsional failure of the instrument 20 is obviated, and any likelihood that the instrument 20 will jam within the canal as it is simultaneously rotated and advanced longitudinally is substantially reduced. Thus, the cutting edges 44, 46 enhance the ease with which the instrument 20, whether a file or a reamer, may be moved longitudinal through a root canal and are advantageous in this respect.

Another advantage provided by the cutting edges 44, 46 and which relates to the reduction in the amount of torsion force needed to rotate the instrument is concerned with the reduction in the amount of strength and material needed by the instrument to resist excessive torsion forces. In other words, since the instrument 20 is not required to withstand excessive tension forces during use, the flutes of the working portion may be grooved deeper so as to reduce the diameter of the instrument core and to enhance the instrument flexibility.

With reference again to FIG. 1, another feature of the instrument 20 is directed to the spacing provided between the adjacent flutes 34, 36 which spiral along the working portion 28. More specifically, there is provided along the length of the working portion 28 a pair of lands 50 of predetermined thickness which extend between the adjacent flutes 34, 36. The width of the lands 50 as measured along the length of the working portion 28 may depend largely upon the pitch and helical angle of the flute 34, 36, but in the illustrated instrument 20 is within the range of 0.003 to 0.007 inches. Each land 50 spirals along the length of the working portion 28 in a helical fashion so that the lands 50 provide the tapered, i.e. conical, periphery of the working portion 28.

It has been found that the provision of the lands 50 between adjacent flutes 34, 36 aids in the proper tracking of the instrument 20 as it is moved in cutting engagement along a surface. In addition, the lands 50 aid in the preservation of prescribed dimensions of the instrument 20, such as instrument diameter, at a preselected cross-section of the working portion 28 during instrument formation so that the peripheral form (e.g. conical form) of the working portion 28 remains uniform and unvarying along its length. With the uniformity in form of the working portion 28 preserved by the lands 50, the instrument 20 provides a relatively clean cut as it is moved through a root canal. More specifically, as the instrument 20 is moved across a surface of the root canal in cutting relationship therewith, the cut surface is devoid of a frayed or frosted appearance.

With reference to FIGS. 5-7, there is illustrated another embodiment, indicated as 56, of an instrument for use as an endodontic file or reamer. The instrument 56 includes a shank 58 having a tapered working portion 64 which extends along a portion of the shank length, and a pilot 62 adjacent the lower end of the shank 58. A fitting 60 is formed in the upper part of the shank 58 for connection to a standardized handle. The working portion 64 of the instrument 56 includes three helical flutes 66, 68, 70 which spiral along the length of the working portion 64 to its leading end 72. Each flute 66, 68, 70 is spaced from its adjacent flute by a land 73 of predetermined thickness and possesses opposing walls 77, 78 which provide the peripheral edges of the working portion 64 with substantially neutral cutting rakes.

As best as shown in FIG. 6, the leading end 72 of the working portion 64 lies in a plane oriented substantially perpendicular to the longitudinal axis 74 of the shank-like body 58, and one wall 78 of each flute 66, 68 or 70 terminates at the leading end 72 in a cutting edge 76. Each cutting edge 76 lies in the plane of the leading end 72 and, due to the shape of the wall 78, which is gradually sloped upwardly as a path is traced radially inwardly from the periphery of the working portion 64, is arcuate in shape as best illustrated in FIG. 7.

The foregoing detailed description is given primarily for understanding of the invention and no unnecessary limitations are to be understood therefrom for modifications will become obvious to those skilled in the art upon reading this disclosure and may be made without departing from the spirit of the invention and the scope of the appended claims.

What is claimed is:

1. An endodontic instrument, such as a reamer or file, comprising an elongated shank including:

a working portion extending along a section of the length of said shank and having a leading end and being tapered in shape so that its diameter decreases in size as a path is traced along the working portion toward the leading end, said working portion including at least one continuous helical flute which spirals along the length of the working portion and including a helical land at the periphery of the working portion which extends between adjacent flute sections as a path is traced along the length of the working portion toward the leading end so that the working portion is provided with a central core extending along its length and rib sections joined directly to the central core so as to extend radially outwardly from the core; and a pilot attached to said working portion at the leading end thereof so as to be arranged coaxially with the working portion and which is smaller in diameter than the diameter of said working portion at the leading end;

said working portion further includes at least one lip adjacent the pilot which has a cutting edge which generally lies in a radial plane of the instrument and extends radially outwardly of the working portion from a location adjacent the surface of the pilot to the periphery of the working portion at the leading end thereof, and each flute which spirals along the length of the working portion toward the leading end thereof terminates at the cutting edge of a corresponding lip so that as the instrument is moved longitudinally through a root canal, root canal tissue disposed to one side of the pilot is exposed to the cutting edge of the working portion.

2. The instrument of claim 1 wherein the leading end of the working portion defines a planar surface oriented generally perpendicular to the longitudinal axis of the shank and each flute which spirals along the length of the working portion toward the leading end thereof has a wall which terminates along a cutting edge of the lip adjacent the planar surface so that one side of the cutting edge is provided by the wall of the flute and the other side of the cutting edge is provided by the planar surface of the working portion.

3. The instrument of claim 1 wherein each flute has a wall which meets an adjacent land along a peripheral edge at the periphery of the working portion, and the peripheral edge is provided with a substantially neutral cutting rake.

4. The instrument of claim 1 wherein at least one lip cutting edge is substantially straight.

5. The instrument of claim 1 wherein at least one lip cutting edge is arcuate in shape.

* * * * *